United States Patent [19]

Iio et al.

[11] Patent Number: 5,026,601
[45] Date of Patent: Jun. 25, 1991

[54] ZIRCONIA-BASE SINTERED BODIES HAVING COATING FILMS

[75] Inventors: Satoshi Iio, Konan; Masakazu Watanabe, Nagoya; Toru Imura, Nagoya; Kotaro Kuroda, both of Nagoya; Hiroyasu Saka, Aichi, all of Japan

[73] Assignee: NGK Spark Plug Co., Ltd., Nagoya, Japan

[21] Appl. No.: 165,378

[22] Filed: Feb. 29, 1988

Related U.S. Application Data

[63] Continuation of Ser. No. 749,237, Jun. 27, 1985, abandoned.

[30] Foreign Application Priority Data

Dec. 28, 1984 [JP] Japan .................................. 59-279163

[51] Int. Cl.[5] .......................................... B32B 17/06
[52] U.S. Cl. .................................... 428/336; 123/440; 204/425; 204/426; 429/30; 428/218; 428/334; 428/432; 428/472; 428/688; 428/697; 428/698; 428/701; 428/702
[58] Field of Search ................ 428/432, 688, 697, 698, 428/699, 701, 702, 334, 336, 218, 472; 501/102, 103, 105; 204/425, 426; 123/440; 429/30

[56] References Cited

U.S. PATENT DOCUMENTS

| | | | |
|---|---|---|---|
| 3,977,061 | 8/1976 | Lindstrom et al. | 428/698 X |
| 4,328,296 | 5/1982 | Tanaka et al. | 501/103 |
| 4,360,598 | 11/1982 | Otagiri et al. | 501/103 |
| 4,500,412 | 2/1985 | Takahashi et al. | 204/425 |
| 4,510,036 | 4/1985 | Takeuchi et al. | 204/425 |
| 4,522,633 | 6/1985 | Dyer | 428/698 X |
| 4,544,607 | 10/1985 | Kaneno et al. | 428/472 |
| 4,598,028 | 7/1986 | Rossing et al. | 429/30 |
| 4,601,809 | 7/1986 | Kitahara | 204/425 |
| 4,642,174 | 2/1987 | Shibata | 204/425 |
| 4,776,943 | 10/1988 | Kitahara | 204/426 |

OTHER PUBLICATIONS

EP 0166445, Jan. '86, Kogima 428/701.
Digest of Proceedings of the Spring Conference 1984 at Kyoto, 22–24 May 1984, Powder and Powder Metallurgy Association (Japan), Low-Temperature Degradation of PSZ Toyota Central Research & Development Labs., Inc.

Primary Examiner—Ellis P. Robinson
Assistant Examiner—Archene A. Turner
Attorney, Agent, or Firm—Fish & Richardson

[57] ABSTRACT

A zirconia-base sintered body comprising a sintered substrate containing 30% by volume or more of tetragonal zirconia and a coating film disposed thereon, characterized in that the diffusion coefficient of oxygen in a material forming said coating film at no higher than 550° C. is smaller than that of oxygen in said tetragonal zirconia at a temperature of no higher than said temperature.

9 Claims, 1 Drawing Sheet 1. polycrystalline alumina
2. $Y_2O_3$-stabilized zirconia

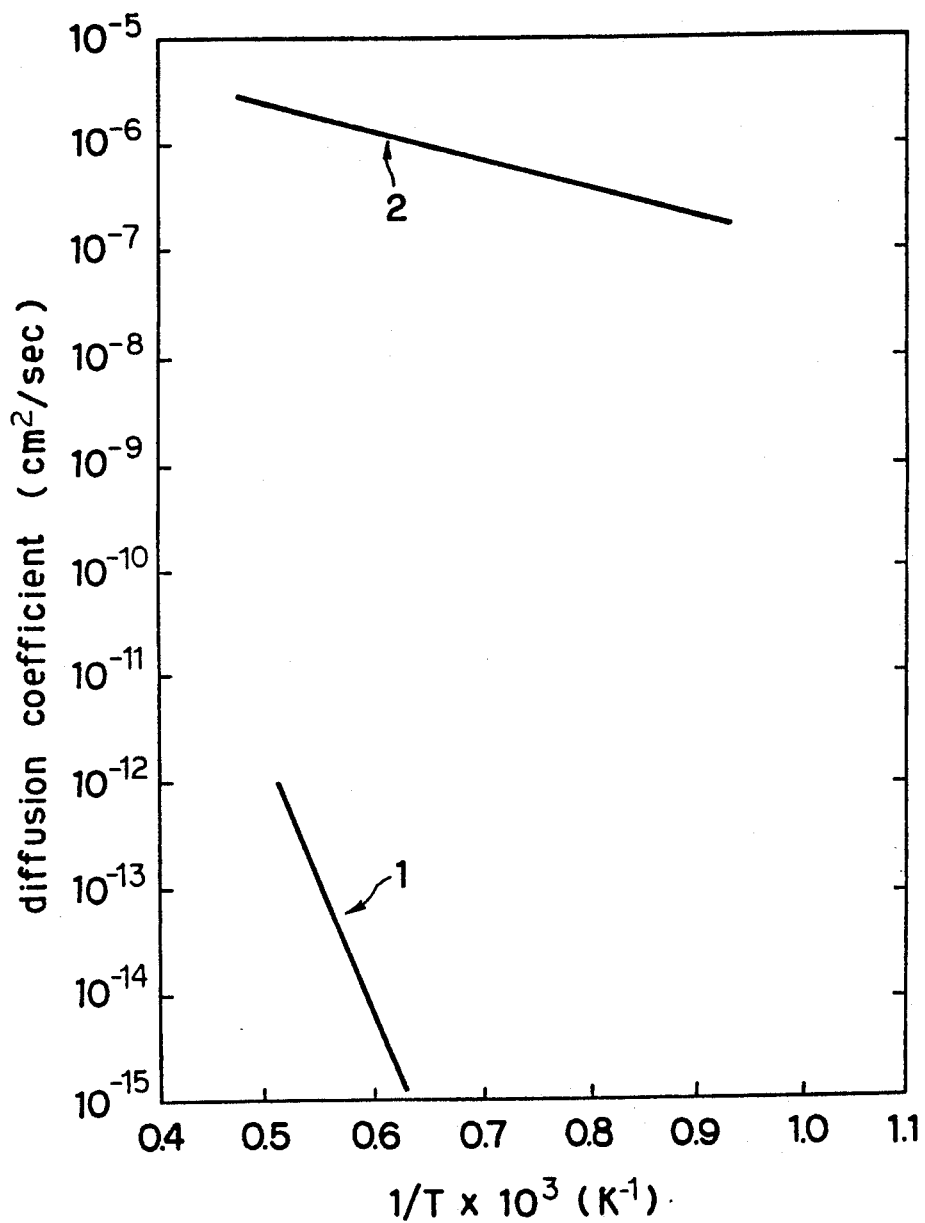
1. polycrystalline alumina
2. $Y_2O_3$-stabilized zirconia 5,026,601

ZIRCONIA-BASE SINTERED BODIES HAVING COATING FILMS

This application is a continuation of U.S. application Ser. No. 749,237, filed June 27, 1985, now abandoned.

FIELD OF THE INVENTION

The present invention relates to a zirconia-base sintered body having a coating film, which is used as the structural material required to have high strength, high toughness, heat insulation or heat reasistance such as parts for internal combustion engines or as the nonsensitive supporting portion of function elements required to have oxygen sensitivity, e.g., oxygen sensor elements or the like.

BACKGROUND OF THE INVENTION

Due to their high strength and toughness, attention is now paid as the structural materials to partially stabilized zirconia sintered bodies (hereinafter referred to as the PSZ sintered bodies) in which the tetragonal zirconia of a metastable phase remains, as well-known in the art, or composite sintered bodies of the partially stabilized zirconia with other ceramics. Similar attention is also paid to the fact that they can be used as the function elements that are used under severe conditions due to the oxygen sensitivity zirconia per se possesses. However, the PSZ sintered bodies have offered a problem in connection with durability, and have been only used in limited fields. This is because the gradual transformation of the tetragonal zironia to the monoclinic zirconia takes place at a temperature of 200°–400° C. with the accompanying drop of mechanical strength. In order to provide a solution to this problem, it has been proposed to apply a water-resistant coating film on the surface of the PSZ sintered bodies with effectiveness. Such proposal has been disclosed in an article entitled "Low Temperature Deterioration of PSZ", Preliminary Transactions of the Spring Conference of 1984, page 122, Japan Society of Powder and Powder Metallurgy. The means disclosed in the aforesaid Preliminary Transactions has been based on the findings that the transformation of the tetragonal to monoclinic zirconia results from moisture present in an atmosphere.

SUMMARY OF THE DISCLOSURE

As a result of intensive studies made by the present inventors, however, it has been found that, with the PSZ sintered bodies, there still occurs a drop of strength even in dry air in association with the transformation phenomenon.

It is therefore a primary object of the present invention to provide a novel zirconia-base sintered body with a coating film which can eliminate the aforesaid drawbacks in the prior art.

Based on further studies it has turned out that the cause for such drop closely correlate with the solid-solution formation and diffusion of the atmospheric oxygen with and into the tetragonal zirconia.

The present invention has been accomplished in view of such situations, and has for its specific object to provide a zirconia-base sintered body provided with a coating film in which a sintered body comprising no less than 30% by volume of the tetragonal zirconia and the balance of other type ceramics different from said tetragonal zirconia is used as the substrate, and said substrate is applied on its surface with a coating film meeting the certain requirement, thereby allowing said zirconia-base sintered body to have improved durability without causing any drop of strength in association with the transformation phenomenon.

According to the present invention, the object is achieved by the following means: As the coating film, use is made of a material having a diffusion coefficient of oxygen at a temperature of no higher than 550° C., which is smaller than that of the tetragonal zirconia at a temperature of no higher than said temperature.

The reasons why the substrate to be applied on the surface with the coating film is limited to a sintered body containing the tetragonal zirconia in an amount of 30% by volume or higher in the present invention are that, unless the content of the tetragonal zirconia reaches 30% by volume, the high toughness peculiar to the PSZ sintered body is not attained and the rate of occurrence of phase transformation is so very low that the need of forming any coating layer is reduced or eliminated. However, it is understood that the present invention is more suitable for the substrate containing higher tetragonal zirconia, e.g., 50%, 80%, 90%, 99% or more by volume.

Although the phase transformation mechanism of the tetragonal zirconia (hereinafter referred to as the t-$ZrO_2$) to the monoclinic zirconia (hereinafter referred to as the m-$ZrO_2$) still seems to involve uncertain factors, the main factor is that the atmospheric oxygen forms solid-solution with and diffuses into the t-$ZrO_2$ which contains a large number of oxygen vacancies and is of a metastable phase in a temperature range of 200° to 400° C. resulting in its transformation to the stable m-$ZrO_2$ phase. The coating film, that is one of the constructional requirements of the present invention, functions to cut off the penetration of oxygen into the t-$ZrO_2$, thereby preventing it from such phase transformation.

This action becomes prominent, where the t-$ZrO_2$ in the substrate is partially stabilized by allowing it to contain as stabilizer at least one selected from $Y_2O_3$ and $Yb_2O_3$ and, if desired, include another stabilizer (different from the first two stabilizers).

Reference will now be made to the reasons for limiting the coating film applied to a material, the oxygen diffusion coefficient of which has the aforesaid relation to the oxygen diffusion coefficient in the t-$ZrO_2$ material. If the oxygen diffusion coefficient in the coating film is equal to or larger than that in the t-$ZrO_2$, the atmospheric oxygen then penetrates easily into the t-$ZrO_2$ through the coating film, thus making a contribution of the phase transformation. In consequence, the function-to-cut-off-oxygen of the coating film, that is one of the essential requirements of the present invention, is not produced. The larger the difference in both coefficients of diffusion, the better the function-to-cut-off-oxygen.

The difference in the diffusion coefficient of oxygen should preferably be by at least $10^3$, more preferably $10^5$, $10^6$ or more.

Reference will then be made to the reasons why the correlation of both diffusion coefficient is defined in the aforesaid temperatures. Since the temperature range within which the occurrence of the phase transformation takes place is between 200° C. and 400° C., limitation may sufficiently be placed only upon the relation appearing within such a range so as to prevent the phase transformation. For the completeness of the action and due to the fact that an extremely extended period of time is required to measure the diffusion coefficient (for instance, a period on the order of several months to several years is required to measure the diffusion coefficient at 550° C.), the present invention is limited to the relation appearing at temperatures of no higher than 550° C. so as to define more clearly the technical scope of the present invention. It is to be understood that the best way to measure the diffusion coefficient is effected within the temperature range of 200° C. to 400° C. In the event that it is very difficult to measure the diffusion coefficient depending upon the aforesaid time factor, however, use may be made of the linear relation established between the inverse number of absolute temperature and the diffusion coefficient, as illustrated in the single drawing. That is, the the diffusion coefficient at 200° to 400° C. may be determined from the gradient of the linear line and the values of the diffusion coefficient at 550° C. or higher temperatures by extrapolation.

BRIEF DESCRIPTION OF THE DRAWING

The single drawing is a graph showing the relationship between the diffusion coefficient of oxygen in polycrystalline alumina or yttria-stabilized zirconia and the inverse number of absolute temperature.

For the convenience of illustration, the drawing shows one example of the diffusion coefficient with the inverse number of absolute temperature as abscissa and the diffusion coefficient as ordinate. Reference numeral 1 stands for the linear line showing the relation between the inverse number of absolute temperature and the diffusion coefficient of oxygen in polycrystalline alumina, and 2 indicates the linear line showing the relation between the inverse number of absolute temperature and the diffusion coefficient of oxygen in yttria stabilized zirconia.

As mentioned in the foregoing, even upon extended exposure to a temperature range in which the phase transformation of the conventional PSZ sintered bodies would take place, the invented zirconia-base sintered bodies having thereon the coating films can maintain their strength with improved durability without suffering any phase transformation.

PREFERRED EMBODIMENTS

As mentioned above, the coating film according to one of the requirements of the present invention functions to cut off oxygen with respect to the substrate. However, where said coating film is less than 0.1 micron thickness, it does not prominently function. Thus, it is desired that said coating film has a thickness of 0.1 micron or more (more preferably 1 μm or more) and the highest performance is attained at 5 μm or more. The film thickness of 5 μm appears to be sufficient, however, may be up to 100 μm depending upon the desired performance.

For the coating film that is one of the constructional requirements of the present invention, any materials such as ceramics, glasses and these composite materials may be used, as long as they do not depart from the gist of the present invention. However, proper selection may preferably be made in order to allow the coating film to have excellent properties in respect of mechanical strength, heat resistance and thermal shock resistance, which are demanded according to the purpose of the sintered bodies of the present invention. Among others, preference is given to thermally resistant and oxidation-resistant materials, such as glasses having a softening point of no lower than 600° C., metal carbides, metal nitrides, metal borides or metal oxides having similarly a melting point of no lower than 600° C., or solid solutions thereof. Typically, these are exemplified by $Al_2O_3$, $Cr_2O_3$, SiC, TiC, WC, $Si_3N_4$, TiN, AlN, $TiB_2$ and the like. The coating film may be formed by an appropriate technique suitably selected depending upon the film material. In general, the deposition technique such as CVD, PVD (sputtering etc.) is typical ones. Thermal application (firing) for the film coating to follow dipping, spray coating, screen printing or the like green film coating may be selected.

The coating film may also be of a double- or more-layer laminate-structure wherein the first layer is formed of a material showing satisfactory adhesion to the substrate and having a coefficient of thermal expansion close to that of the substrate. A composite layer structure of the above materials or these with a metal layer or the like may be applied.

EXAMPLES

In the following, the present invention will more concretely be explained with reference to the examples.

$ZrO_2$ powders prepared by co-precipitation, containing 2 mol % of $Y_2O_3$ and having a mean particle size of 0.1 micron were rubber-pressed at a pressure of 1500 kg/cm², and sintered at 1550° C. for 1 hour in the atmosphere, to thereby obtain PSZ sintered bodies having a t-$ZrO_2$ content of 99% by volume or higher, a mean crystal grain size of 1.0 micron and a size of 3×4×40 mm (This was also used as a zirconia-base sintered body R1 having no coating film for the purpose of comparison). Used as the substrate, this PSZ sintered body was applied on the surface with coating films of $Al_2O_3$ having the thickness as specified in Table 1 at a temperature of 1000°–1100° C. and a pressure of 100 Torr by means of chemical vapor deposition (hereinafter referred to as the CVD), to thereby prepare the invented zirconia-base sintered bodies 1–6 having thereon the coating film as well a zirconia-base sintered body R2 for comparison. The invented zirconia-base sintered bodies 1–6 as well as the zirconia-base sintered bodies R1 and R2 for comparison were aged at 300° C. for 1000 hours in dry air passed through silica gel so as to measure the density and mechanical strength thereof as well as the amount of the m-$ZrO_2$ formed on the surface of the substrate in the following procedures before and after aging. The results are set forth in Table 1.

MEASUREMENT OF DENSITY

Apparent density was measured according to the Archimedean method.

MEASUREMENT OF MECHANICAL STRENGTH

Bending strength was measured according to JIS Standard R1601, and the measurements of five samples were averaged.

MEASUREMENT OF THE AMOUNT OF m-$ZrO_2$ OCCURRED

The amount of m-$ZrO_2$ occurred in the samples before aging was measured in the following procedures. Before the application of the coating film, the substrate was mirror-polished with a diamond paste of 15 microns. Thereafter, that substrate was set on a Geiger Flex RAD-αA type X-ray diffractometer for X-ray diffraction (manufactured by Rigaku Denki Co., Ltd.), to thereby measure the integrated intensities of the planes [11$\bar{1}$] and [111] of the m-$ZrO_2$, the plane [111] of the t-$ZrO_2$ and the plane [111] of the cubic zirconia (hereinafter referred to as the c-$ZrO_2$), designated in terms of Im, It and Ic in that order. The amount of m-$ZrO_2$ formed was determined from the ratio between Im and (Im+It+Ic). The amount of m-$ZrO_2$ formed in the samples after aging was measured in the following procedures. The coating films on the surface of the substrate were polished off by means of a diamond paste of 15 microns. That amount was then determined from the ratio between Im and (Im+It+Ic), like the samples before aging.

It is to be noted that the t-$ZrO_2$ content of the samples was measured in the following procedures. After the determination of the amount of m-$ZrO_2$ occurred, the substrate was pulverized to 325-mesh through, and all the t-$ZrO_2$ was transformed into the m-$ZrO_2$ by the mechanical stress produced during pulverization, followed X-ray diffractometry. The c-$ZrO_2$ content was first obtained from the ratio between Ic and (Im+Ic), and the t-$ZrO_2$ content was then determined from the resulting value.

ing the coating films suffer substantially no transformation nor drop of strength.

EXAMPLE 2

BaO-$Al_2O_3$-$SiO_2$-$B_2O_3$ base glass having a coefficient of thermal expansion of $9.82 \times 10^{-6}$ (1/°C.) and a softening point of 806° C. was pulverized to a mean particle size of no higher than 1 micron, and dispersed in ethanol to prepare a glass dispersion liquid. The substrate of the same shape and quality as that of Example 1 was dipped in the glass dispersion liquid, dried, and thermally treated (fired) at 800°–1250° C., to form a glass coating layer resulting in the invented zirconia-based sintered bodies 7 to 12 including thereon the coating films having a thickness as specified in Table 2 and a zirconia-base sintered body R3 for comparison. These bodies were measured under the same conditions as in Example 1 about the density and mechanical strength thereof as well as the amount of m-$ZrO_2$ formed on the surface of the substrate before and after aging. The results are set forth in Table 2.

TABLE 2

| Zirconia-Base Sintered Bodies Having Coating Films | Coating Films | | | Physical Properties of Sintered Bodies | | | | | | |
|---|---|---|---|---|---|---|---|---|---|---|
| | | | Thickness (μm) | Before Aging | | | After Aging | | | |
| | Material | Coating Method | | Density (g/cm³) | Strength (kg/mm²) | m-$ZrO_2$ (vol %) | Density (g/cm³) | Strength (kg/mm²) | m-$ZrO_2$ (vol %) | Presence of Cracks | Remarks |
| R3 | Glass | Firing | 0.05 | 6.06 | 110.3 | 0.4 | 5.89 | 60.8 | 87.1 | Present Observed | Comparison Example |
| 7 | " | " | 0.1 | 6.06 | 108.7 | " | 6.05 | 100.3 | 8.1 | Not Observed | Within Scope of the Invention |
| 8 | " | " | 0.5 | 6.06 | 104.1 | " | 6.05 | 105.5 | 4.3 | Not Observed | |
| 9 | " | " | 1.0 | 6.06 | 102.5 | " | 6.06 | 103.8 | 1.6 | Not Observed | |
| 10 | " | " | 5.0 | 6.05 | 98.2 | " | 6.05 | 102.5 | 0.4 | Not Observed | |
| 11 | " | " | 10.0 | 6.04 | 96.5 | " | 6.04 | 99.7 | " | Not Observed | |
| 12 | " | " | 15.0 | 6.02 | 97.2 | " | 6.02 | 96.5 | " | Not Observed | |

From the results of Table 2, it has been found that the

TABLE 1

| Zirconia-Base Sintered Bodies Having Coating Films | Coating Films | | | Physical Properties of Sintered Bodies | | | | | | |
|---|---|---|---|---|---|---|---|---|---|---|
| | | | Thickness (μm) | Before Aging | | | After Aging | | | |
| | Material | Coating Method | | Density (g/cm³) | Strength (kg/mm²) | m-$ZrO_2$ (vol %) | Density (g/cm³) | Strength (kg/mm²) | m-$ZrO_2$ (vol %) | Presence of Cracks | Remarks |
| R1 | — | — | — | 6.06 | 113.9 | 0.9 | 5.82 | 15.3 | 88.3 | Present Observed | Comparison Example |
| R2 | $Al_2O_3$ | CVD | 0.05 | " | 112.5 | 0.4 | 5.96 | 78.8 | 85.5 | Present Observed | |
| 1 | " | " | 0.1 | " | 111.8 | " | 6.05 | 109.5 | 6.7 | Not Observed | Within Scope of the Invention |
| 2 | " | " | 0.5 | " | 107.1 | " | 6.06 | 108.3 | 3.5 | Not Observed | |
| 3 | " | " | 1.0 | " | 101.4 | " | 6.06 | 100.5 | 1.3 | Not Observed | |
| 4 | " | " | 5.0 | 6.05 | 96.8 | " | 6.05 | 98.3 | 0.4 | Not Observed | |
| 5 | " | " | 10.0 | 6.04 | 95.7 | " | 6.04 | 96.0 | " | Not Observed | |
| 6 | " | " | 15.0 | 6.02 | 95.1 | " | 6.02 | 95.5 | " | Not Observed | |

From the results of Table 1, it has been found that the zirconia-base sintered bodies for comparison give rise to the transformation of the t-$ZrO_2$ to the m-$ZrO_2$ after aging, resulting in a considerable drop of strength, whereas the invented zirconia-base sintered bodies having thereon the coating films suffer no substantial transformation nor drop of strength.

zirconia-base sintered body for comparison gives rise to the transformation of the t-$ZrO_2$ to the m-$ZrO_2$ in the substrate after aging, resulting in a considerable drop of strength, whereas the invented zirconia-base sintered bodies having thereon the coating films suffer no substantial transformation nor drop of strength.

EXAMPLE 3

Sixty (60) % by weight of $ZrO_2$ powders containing a $Y_2O_3$ content of 2 mol % and a mean particle size of 0.1 micron and 40% by weight of $Al_2O_3$ powders having a mean particle size of 0.1 micron were wet-mixed together, and dried. The resulting mixture was rubber-pressed at a pressure of 1500 kg/cm², and sintered at 1550° C. for 1 hour in the atmosphere, to thereby obtain a $ZrO_2$-$Al_2O_3$ composite sintered body having a t-$ZrO_2$ content of 46% by volume (93% by volume calculated based on the $ZrO_2$ particles), a mean crystal grain size of 1.0 micron and a size of 3×4×40 mm. The thus obtained $ZrO_2$-$Al_2O_3$ composite sintered body was used as the substrate, and as a zirconia-base sintered body R4 having no coating film for the purpose of comparison. That substrate was applied on the surface under the same conditions as in Example 1 with the coating films having a thickness as specified in Table 3, to thereby obtain the invented zirconia-base sintered bodies 13 to 18 including thereon the coating films as well as a zirconia-base sintered body R5 for comparison. These samples were measured under the same conditions as in Example 1 for the density and mechanical strength thereof as well as the amount of m-$ZrO_2$ formed on the surface of the substrate. The results are set forth in Table 3.

substrate after aging, resulting in a considerable drop of strength, whereas the invented zirconia-base sintered bodies having thereon the coating films suffer no substantial transformation nor drops of strength.

EXAMPLE 4

The coating films formed of a material as specified in Table 4 were applied onto the surface of the substrate of the same shape and quality as in Example 1 into a thickness as specified in Table 4, to thereby prepare the invented zirconia-base sintered bodies having thereon the coating films. These samples were measured under the same conditions as in Example 1 about the density and mechanical strength thereof as well as the amount of m-$ZrO_2$ formed on the surface of the substrate. The results are set forth in Table 4.

TABLE 4

| Zirconia-Base Sintered Bodies Having Coating Films | Coating Films | | | Physical Properties of Sintered Bodies | | | | | | | |
|---|---|---|---|---|---|---|---|---|---|---|---|
| | | | | Before Aging | | | After Aging | | | | |
| | Material | Coating Method | Thickness (μm) | Density (g/cm³) | Strength (kg/mm²) | m-$ZrO_2$ (vol %) | Density (g/cm³) | Strength (kg/mm²) | m-$ZrO_2$ (vol %) | Presence of Cracks | Remarks |
| 19 | SiC | CVD | 1.0 | 6.06 | 102.2 | 0.4 | 6.06 | 101.5 | 0.8 | Not Observed | Within Scope of the Invention |
| 20 | TiC | " | " | 6.06 | 100.7 | " | 6.06 | 99.8 | 0.9 | Not Observed | |
| 21 | $Si_3N_4$ | " | " | 6.06 | 101.2 | " | 6.06 | 102.4 | 0.7 | Not Observed | |
| 22 | TiN | " | " | 6.06 | 105.1 | " | 6.06 | 103.5 | 0.9 | Not Observed | |
| 23 | AlN | " | " | 6.06 | 103.3 | " | 6.06 | 100.8 | 1.0 | Not Observed | |
| 24 | $TiB_2$ | " | " | 6.06 | 98.5 | " | 6.06 | 99.1 | 0.8 | Not Observed | |

From the results of Table 4, it has been noted that, in the invented zirconia-base sintered bodies having thereon the coating films, there is neither transformation of the t-$ZrO_2$ to the m-$ZrO_2$ in the substrate nor drops of strength after aging.

It should be understood that any modification may be made without departing from the gist of the present invention as disclosed and claimed.

What is claimed is:

1. A zirconia base sintered body comprising a sintered substrate containing 30% by volume or more of tetrago-

TABLE 3

| Zirconia-Base Sintered Bodies Having Coating Films | Coating Films | | | Physical Properties of Sintered Bodies | | | | | | | |
|---|---|---|---|---|---|---|---|---|---|---|---|
| | | | | Before Aging | | | After Aging | | | | |
| | Material | Coating Method | Thickness (μm) | Density (g/cm³) | Strength (kg/mm²) | m-$ZrO_2$ (vol %) | Density (g/cm³) | Strength (kg/mm²) | m-$ZrO_2$ (vol %) | Presence of Cracks | Remarks |
| R4 | — | — | — | 4.96 | 121.3 | 0 | 4.85 | 60.3 | 63 | Present Observed | Comparison Example |
| R5 | $Al_2O_3$ | CVD | 0.05 | 4.96 | 120.1 | " | 4.91 | 85.7 | 58 | Present Observed | |
| 13 | " | " | 0.1 | 4.96 | 119.1 | " | 4.96 | 116.3 | 6.8 | Not Observed | Within Scope of the Invention |
| 14 | " | " | 0.5 | 4.96 | 114.0 | " | 4.96 | 115.5 | 3.3 | Not Observed | |
| 15 | " | " | 1.0 | 4.96 | 108.0 | " | 4.96 | 107.5 | 1.0 | Not Observed | |
| 16 | " | " | 5.0 | 4.95 | 103.0 | " | 4.95 | 100.3 | 0 | Not Observed | |
| 17 | " | " | 10.0 | 4.95 | 102.1 | " | 4.95 | 108.2 | " | Not Observed | |
| 18 | " | " | 15.0 | 4.94 | 101.4 | " | 4.94 | 103.3 | " | Not Observed | |

*1 Amount of m-$ZrO_2$ before and after aging
*2 The amount of m-$ZrO_2$ before and after aging is expressed in terms of the volume percentage with respect to the $ZrO_2$ particles in the sintered bodies.

From the results of Table 3, it has been noted that the zirconia-base sintered bodies for comparison give rise to the transformation of the t-$ZrO_2$ to the m-$ZrO_2$ in the nal zirconia and a coating film of a thickness no less than 0.1 micron disposed thereon, wherein the diffusion coefficient of oxygen in material forming said coating film at a temperature of no higher than 550° C. is at least $10^3$ less than that of oxygen in said tetragonal zirconia at a temperature no higher than said temperature, said sintered body being stable within a range of 200°–400° C. in an oxygen-containing atmosphere.

2. A sintered body as defined in claim 1, in which the material forming said coating film is one selected from the group consisting of glasses having a softening point of no lower than 600° C.; and metal carbides, metal nitrides, metal borides, metal oxides and solid solution thereof having a melting point of no lower than 600° C.

3. A sintered body as defined in claim 1, in which said coating film is of a multi-layer structure wherein different materials are laminated on each other.

4. A sintered body as defined in claim 1, in which said tetragonal zirconia in said substrate is partially stabilized.

5. A sintered body as defined in claim 2, in which said coating film is formed of one or more selected from the group consisting of $Al_2O_3$, $Cr_2O_3$, SiC, TiC, WC, $Si_3N_4$, TiN, AlN, $TiB_2$ and a solid solution thereof.

6. A sintered body as defined in claim 1, in which the difference in the diffusion coefficient of oxygen is at least $10^5$.

7. A sintered body as defined in claim 5, in which said tetragonal zirconia is partially stabilized by a stabilizer of at least one selected from the group consisting of $Y_2O_3$ and $Yb_2O_3$.

8. A zirconia base sintered structural element for an internal combustion engine, comprising a sintered substrate containing 30% by volume or more of tetragonal zirconia and a coating film of a thickness no less than 0.1 micron disposed thereon, wherein the diffusion coefficient of oxygen in material forming said coating film at a temperature of no higher than 550° C. is smaller than that of oxygen in said tetragonal zirconia at said temperature by at least $10^3$.

9. A zirconia base sintered nonsensitive supporting element for an oxygen sensor for use in an internal combustion engine, comprising a sintered substrate containing 30% by volume or more tetragonal zirconia and a coating film of a thickness no less than 0.1 micron disposed thereon, wherein the diffusion coefficient of oxygen in material forming said coating film at a temperature of no higher than 550° C. is smaller than that of oxygen in said tetragonal zirconia at said temperature by at least $10^3$.

* * * * *